US 6,749,399 B2

(12) United States Patent
Heronemus

(10) Patent No.: US 6,749,399 B2
(45) Date of Patent: Jun. 15, 2004

(54) VERTICAL ARRAY WIND TURBINE

(75) Inventor: William E. Heronemus, Amherst, MA (US)

(73) Assignee: Ocean Wind Energy Systems, Newton, MA (US)

( * ) Notice: Subject to any disclaimer, the term of this patent is extended or adjusted under 35 U.S.C. 154(b) by 0 days.

(21) Appl. No.: 10/092,775

(22) Filed: Mar. 7, 2002

(65) Prior Publication Data

US 2003/0170123 A1 Sep. 11, 2003

(51) Int. Cl.[7] .................................................. F03D 1/02
(52) U.S. Cl. ............................. 416/41; 416/44; 416/120
(58) Field of Search ........................... 416/44, 41, 120; 290/55

(56) References Cited

U.S. PATENT DOCUMENTS

| 4,068,132 A |   | 1/1978  | Bardekoff |        |
|-------------|---|---------|-----------|--------|
| 4,220,870 A |   | 9/1980  | Kelly     |        |
| 4,265,086 A |   | 5/1981  | Bahrenburg|        |
| 4,285,481 A |   | 8/1981  | Biscomb   |        |
| 4,340,822 A |   | 7/1982  | Gregg     |        |
| 4,410,806 A | * | 10/1983 | Brulle    | 290/44 |
| 4,550,259 A |   | 10/1985 | Bertels   |        |
| 4,651,017 A | * | 3/1987  | Longrigg  | 290/44 |
| 4,735,552 A |   | 4/1988  | Watson    |        |
| 5,146,096 A |   | 9/1992  | McConachy |        |
| 5,182,458 A |   | 1/1993  | McConachy |        |
| 5,876,181 A |   | 3/1999  | Shin      |        |
| 5,969,430 A |   | 10/1999 | Forrey    |        |
| 6,100,600 A |   | 8/2000  | Pflanz    |        |

FOREIGN PATENT DOCUMENTS

| DE | 742242        | 5/1943  |
| DE | 2138500       | 8/1971  |
| DE | 41 01 591 A1  | 1/1991  |
| DE | 42 36 092 A1  | 10/1992 |
| DE | 195 13 321 A1 | 4/1995  |
| WO | WO 98/00639   | 1/1998  |

OTHER PUBLICATIONS

Jamieson, Multi Rotor Systems, ETSU Report W/23/00355/REP, pp. 21 to 39 plus figures, 1995.

* cited by examiner

Primary Examiner—Edward K. Look
Assistant Examiner—Kimya N McCoy
(74) Attorney, Agent, or Firm—John Vanden Bosche

(57) ABSTRACT

A wind turbine with an array of rotors arranged at various heights. Each rotor is optimized for the height at which it is located. Optimization of each rotor could include selection of rated power, solidity, tip speed, blade twist, blade taper, or rotor diameter. Each rotor can also be operated in a manner that is optimized for the wind speed it experiences. Optimized operation parameters could include blade pitch angle or rotor speed.

4 Claims, 16 Drawing Sheets

VERTICAL ARRAY WIND TURBINE

FIELD OF THE INVENTION

The invention relates to the field of wind turbine generators. Specifically, the invention relates to an array of wind turbine rotors on a single tower that are individually optimized to improve the economics of the entire system.

BACKGROUND OF THE INVENTION

Wind turbines have gained widespread use for electricity generation in recent years. The cumulative capacity of wind turbines installed worldwide has grown at a rate of approximately 32% per year over the past ten years. As of the end of 2001, the total installed capacity of wind turbines worldwide added up to over 20,000 MW. Future growth prospects for the industry are bright, although the economics of wind energy must continue to improve for the market to grow. There are signs that the potential for economic gains from current wind turbine technology is constrained.

As the market for wind turbines has grown in recent years, the size of the turbines has also grown. FIG. 1 shows the typical rotor diameter and rated power for state of the art wind turbines that have been installed in Europe over the past 15 years. Most wind turbine manufacturers have recently introduced turbine designs in the range of 1.5 to 2.5 MW with rotor diameters of 66 to 80 m. Even larger turbines are on the drawing boards of most wind turbine manufacturers. The trend toward larger turbines has been driven partly by technological and economic improvements, but the trend has largely been driven by market demand. Bigger wind turbines have proven to be more productive than smaller designs, largely due to the taller tower heights of the larger machines. Also, there is an economy of scale that favors large turbines because there are certain fixed costs associated with road construction, project planning, SCADA equipment, and operations and maintenance that do not increase with larger turbines. However, large turbines are also considerably more expensive than smaller machines and the economy of scale does not completely explain the trend to multi-megawatt size wind turbines. Project developers have demanded larger wind turbines at least partly due to perception issues. In Europe, where population density is relatively high compared to the United States, it is easier to obtain permits for fewer large turbines compared to a larger number of small turbines. Also, as wind turbines are installed offshore, there is a growing market for very large turbines to be used in that market.

As the size of wind turbines grows, there are several technical issues that adversely affect the economics of wind energy and that can potentially lead to constraints in turbine size. Basic design principles indicate that the weight of the turbine increases approximately with the cube of the rotor diameter. System cost is generally proportional to the turbine's weight and so the cost of the turbine increases approximately with the rotor diameter cubed. The turbine weight and cost increase faster than the energy capture, which increases with the rotor diameter squared. For relatively small turbine sizes, there are other economies of scale that outweigh the increase in turbine weight and cost, however for turbines over approximately one megawatt in size the economies of scale are outweighed.

Another problem with large wind turbines is blade deflection. The wind turbine rotor is typically oriented upwind of the tower so that the blades bend downwind toward the tower. The turbine designer must take care so that the blade does not strike the tower, thereby causing catastrophic failure. The blade's stiffness, defined by the material modulus of elasticity multiplied by the cross-sectional moment of inertia, or EI, increases as the blade becomes longer. However, the loads that cause deflection also increase for longer blades. If all of the blade's dimensions are scaled proportionately to the blade length, then EI increases with the blade length to the fourth power whereas the bending moment increases with the blade length to the third power. This would lead to lower deflection for longer blades. However, practical considerations such as tooling, blade weight, and material cost constrain the design so that the blade's chord and thickness are smaller relative to the blade's length for large rotors. This causes a higher aspect ratio and lower solidity for large rotors. The lower solidity requires a higher tip speed for good aerodynamic performance and the higher tip speed can lead to increased centrifugal stiffening of the blade which reduces blade deflection. However, noise issues tend to constrain tip speed ratio so that centrifugal stiffening is less for very large rotors. Deflection thereofore becomes the design driver for very large rotors. Blade deflection can be mitigated by using large uptilt of the wind turbine nacelle. However, wind turbine designers are already using high (7 degrees) uptilt and negative coning to avoid tower strikes. Some blades are even being built curved to incorporate effective negative coning. All of this points toward blade deflection becoming a limiting design criteria for very large wind turbine rotors.

Another issue with very large rotors is that there is a large amount of composite material in each blade which can lead to material problems. Statistically, there is a higher probability of a defect existing in a large blade than in a small blade. If a defect is built into a blade, it can propogate to become a crack which will eventually lead to the blade's failure. As the thickness of the blade's laminate increases, it becomes more and more difficult to detect flaws in the material. Therefore, very large wind turbine blades may have a higher statistical probability of failure than a larger number of smaller blades.

Another issue for very large wind turbines is transportation and installation logistics. The long blade lengths being used on multi-megawatt wind turbines can exceed the capacity of public roads. Also, the tower heights necessary to support the large rotors can exceed the height capacity of cranes that are readily available.

Another problem experienced by the large wind turbines that are currently under development or being sold is that the rotors are so large that they experience a massive differential in wind speed from one side of the rotor to the other. Vertical wind shear exponents in the Midwest have been measured as high as 0.40 which can cause the wind speed across a 70 m rotor to vary by 62% from bottom to top if the turbine is mouted on a 65 m tower. The variation in wind loading is even more severe since loads are generally proportional to wind speed squared. In the example given, the bending load due to the wind at the top of the rotor would be 262% higher than the bending load due to the wind at the bottom of the rotor. Since each blade moves through this shear field, they are subjected to extreme fatigue loading conditions. From an energy standpoint, things are even worse. Energy in the wind is proportional to wind speed cubed which means that the energy content in the wind at the top of the rotor is 425% higher than the energy content at the bottom of the rotor.

Since all of the blades have the same rotational speed and pitch angle, it means that the entire rotor must be optimized for an average wind that is "seen" by the entire rotor. The rotor speed and blade pitch that work best for the wind speed at the rotor's center may not work well at all for the portions of the rotor at the top and bottom. Therefore, at least part of the rotor will be operating in a sub-optimal condition whenever a wind shear is present. This problem is made worse as the turbine's rotor diameter gets larger.

The issue of windspeed variation across the rotor also has negative implications for selecting an appropriate turbine for a given site. Wind turbine manufacturers generally offer their equipment with a range of rotor diameters for a given power rating or, conversely, with a range of power ratings for a given rotor diameter. For example, a 750 kW turbine may be sold with an option for a 46 m, 48 m, or 50 m rotor for high wind, moderate wind, and low wind sites respectively. Conversely, a company may offer a variety of power trains and generators with various power ratings for a turbine with a fixed rotor size. For example, a wind turbine with a 48 m rotor may be sold as a 600 kW, 700 kW, or 800 kW turbine for low speed, moderate speed, or high wind speed sites respectively. When the wind turbine's rotor grows to be very large, it is more difficult to tailor the power rating and rotor diameter to fit the site. A turbine with a 70 m rotor diameter may experience an annual average wind speed of 6 m/s at the bottom tip of the rotor, 8 m/s at hub height, and 10 m/s at the upper tip of the rotor. Based on the annual average wind speed at the bottom tip of the rotor the turbine should be optimized for a low wind speed site, based on the annual average wind speed at hub height the turbine should be optimized for a moderate wind speed, and based on the annual average wind speed at the upper tip of the rotor the turbine should be optimized for a high wind speed site. Whichever rotor is selected, it will not be optimized for the entire rotor disk area.

As wind turbines grow very large there are several problems which need to be solved. First, the weight and cost of the turbine grow disproportionately for a very large rotor diameter. It would be desirable to provide a multi-megawatt wind turbine with a weight per unit of rotor swept area that is comparable to smaller turbine designs. Second, blade deflection becomes a problem and limits the rotor design for very large wind turbines. It would be desirable to provide a multi-megawatt wind turbine in which blade deflection is not a problem. Third, large wind turbine rotors have a greater statistical probability of material defects in the blades compared to smaller wind turbines. It would be desirable to provide a multi-megawatt wind turbine that does not require massive amounts of material in the blade roots leading to higher statistical probability of material defects. Fourth, transportation and construction logistics are problematic for very large wind turbines. It would be desirable to provide a multi-megawatt wind turbine that does not utilize massive blades and other components so that they can be easily transported and erected. Fifth, large wind turbines experience massive wind speed variations across their rotors so that at least a portion of the rotor is likely to be operating in sub-optimal conditions for the wind speed it is experiencing. It would be desirable to provide a multi-megawatt wind turbine in which the entire rotor area is optimized for the wind speed that it "sees."

SUMMARY OF THE INVENTION

The present invention solves the problems of the prior art wind turbines by utilizing a plurality of smaller rotors mounted on a single tower. The rotors are at various heights on the tower so that they each "see" different wind speeds. Accordingly, each rotor is optimized for its wind speed.

The individual rotors are more cost-effective than one massive rotor in that the combined weights and costs of the plurality of small rotors are less than the weight and cost of one massive rotor. Furthermore, because the rotors are mounted on a single tower, only one foundation, access road, and electrical connection are required, thereby providing cost savings over a plurality of smaller turbines on individual towers. Therefore, the turbine of the present invention provides the economy of scale that can be obtained with a very large turbine, but it also avoids the disadvantages associated with a massive rotor.

Another advantage of the present invention is that each of the plurality of rotors is optimized for its individual wind regime. Each rotor can have a unique power rating relative to its swept area. In this way, the blades, hubs, pitch assemblies, and main bearings are similar for all of the rotors and are interchangeable as spare parts. However, the drive train and generator for each rotor would be unique. Other parameters that could be optimized for each rotor include its solidity and tip speed, although if the rotors are to be interchangeable then the solidity must be consistent among rotors. Generally, the rotors toward the top of the tower have a higher power rating, a higher tip speed, and optionally a lower solidity. This allows each rotor to extract the maximum possible amount of energy out of the wind for the wind resource that it "sees." The energy extracted by a plurality of small rotors is greater than the energy extracted by a single massive rotor because each of the smaller rotors can be better tailored to its unique wind resource.

Each of the rotors is also controlled individually for the local wind speed that it experiences. Control parameters can include cut-in, cut-out, rotor speed, and blade pitch. By controlling each rotor individually it is possible to achieve a higher overall efficiency compared to controlling a single massive rotor based on the average wind speed that the rotor sees. Each rotor is controlled to be at the appropriate rotor speed and blade pitch to maintain peak efficiency. This allows the entire system to operate at peak efficiency for the entire range of wind speeds experienced from the lowest rotor to the highest rotor. In contradistinction, a single large rotor can only be controlled to operate at peak efficiency for one height and one wind speed while much of the rotor operates at lower efficiency.

The present invention has further advantages in terms of availability and maintenance. When a very large wind turbine faults offline, its entire production is lost. In contrast, one of the rotors of the present invention can fault offline with the resulting loss of only a small fraction of the total output. For example, if a 1.5 MW wind turbine experiences a blown fuse or some other relatively minor failure, the entire turbine is shutdown with the loss of 1.5 MW of power production. A comparable wind turbine system according to the present invention may include 15 rotors each with an output of 100, 200, 300, or 400 kW upon each rotor's hub height in the vertical array. If a fuse or other minor part fails even in the uppermost rotor, then the lost output is only 400 kW and the system can continue to produce 3500 kW out of the total system rated power of 3900 kW.

From a maintenance point of view, the present invention's larger number of small rotors allows the operators to keep a more complete selection of spare parts. For instance, if an operator is in charge of a 30 MW wind farm that consists of 20 turbines each rated at 1.5 MW they are not likely to keep any spare blades, generators, or gearboxes on hand. If one of those components experiences a failure, the operator must wait for the turbine manufacturer to supply another part and the turbine may be shut down for weeks. By contrast, if the operator was in charge of a 30 MW wind farm consisting of 20 turbines according to the present invention where each turbine has 15 rotors rated at 100 to 400 kW each, the operator would have a total of 300 sets of blades, generators, and gearboxes in operation. He could more easily justify having a spare set of components on hand because the cost of the set of spares would be lower in relation to the total cost of the wind farm.

Another maintenance advantage of the present invention is that it does not require a massive crane as prior art turbines do. Turbines that are being erected today in the 1.5 to 2 MW size range require cranes with capacities of over 500 tons that are very expensive to mobilize. By comparison, each of the smaller rotors on the wind turbine of the present invention can be lifted using a much smaller crane that is locally available and can be mobilized for a small fee. Maintenance can be further facilitated if each array of wind turbine rotors includes a boom-car crane. The boom-car crane could be located on top of the tower and could be used to remove and replace any of the rotors without the assistance of a separate crane.

BRIEF DESCRIPTION OF THE DRAWINGS

Other features and advantages of the invention will be apparent from the following Detailed Description taken in conjunction with the accompanying drawings, in which.

DETAILED DESCRIPTION OF THE INVENTION

Figure 1:
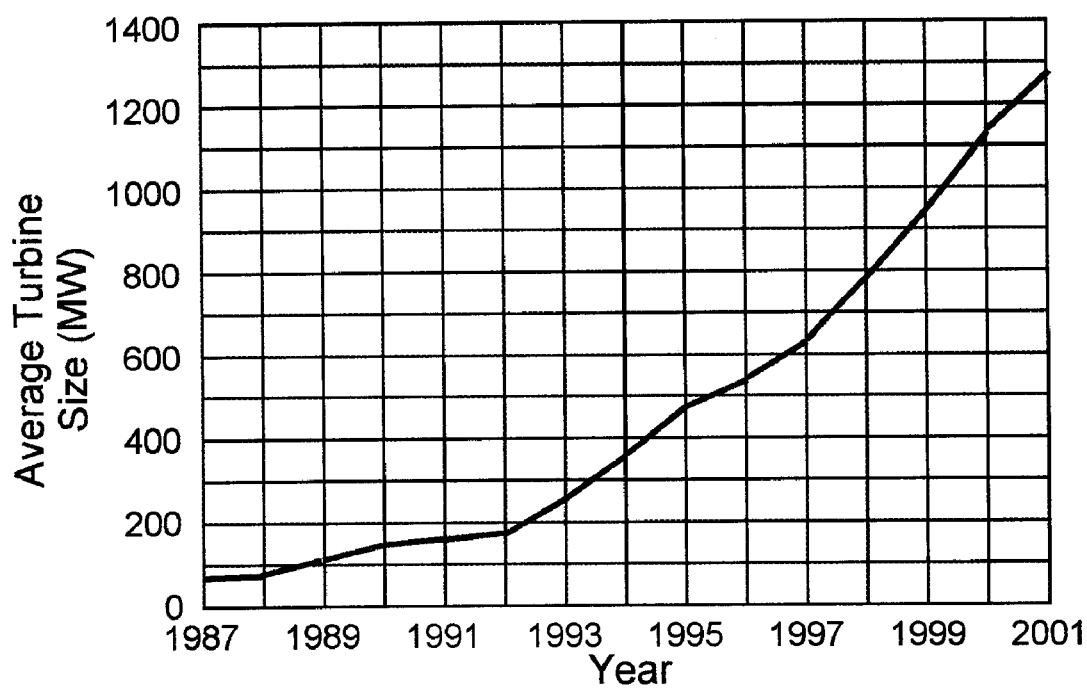
FIG. 1 is a graph showing the trend toward larger wind turbine rotors in recent years.
Figure 2:
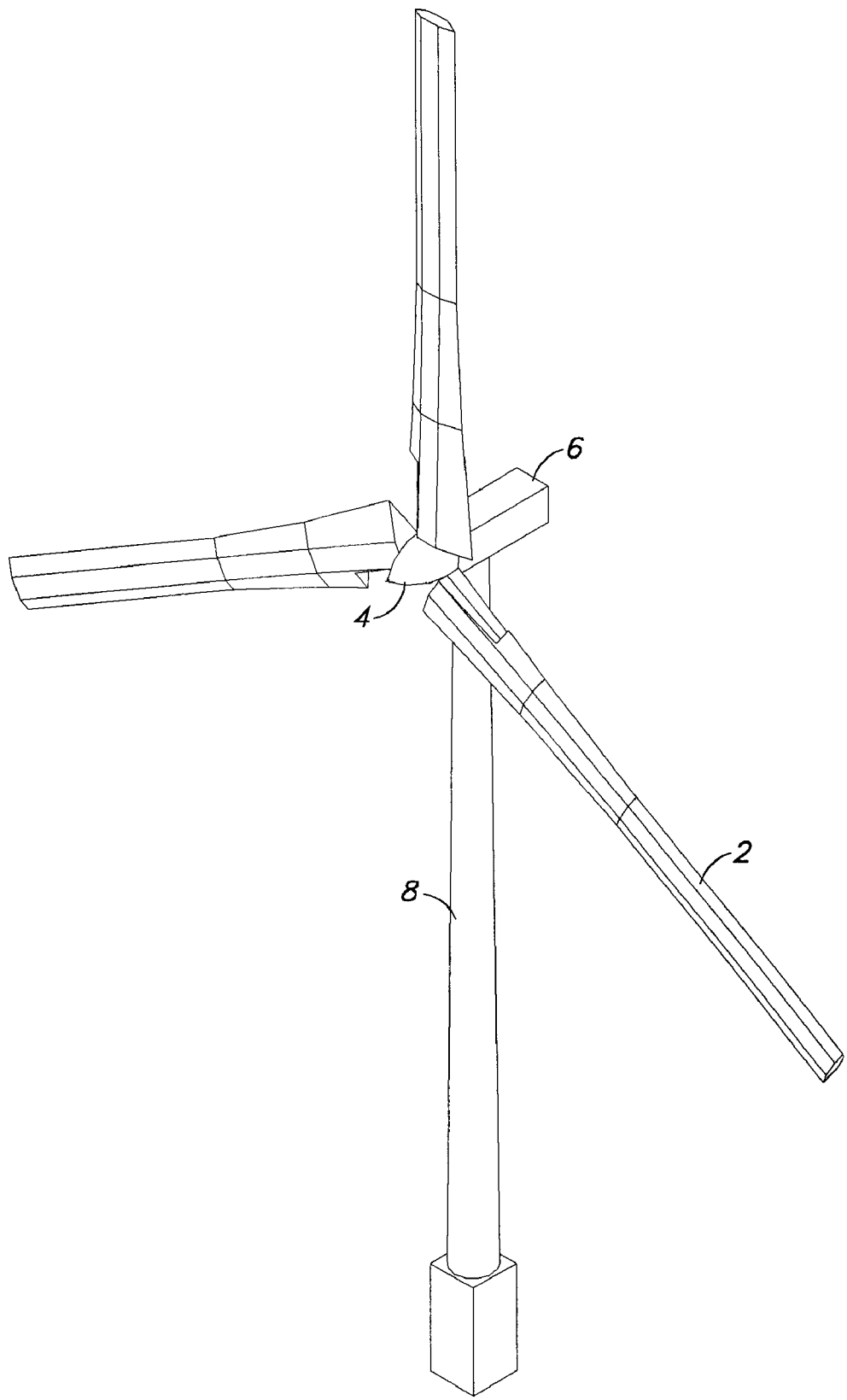
FIG. 2 is a prior art wind turbine.

FIG. 2 shows a wind turbine according to the prior art. The turbine includes a set of blades 2, a hub 4 a nacelle 6, and a tower 8. Prior art turbines can include any number of blades 2, although three blades is the most common configuration. The blades 2 can be oriented upwind or downwind of the tower 8, although upwind is the most common and most efficient configuration. A yaw system is provided to allow rotation between the nacelle 6 and the tower 8 so that the nacelle 6 can be aligned with the wind direction. The rotor diameter is defined as two times the length of a blade 2 plus the diameter of the hub 4. Typical rotor diameters for commercially available wind turbines have grown significantly over the past 15 to 20 years. In the mid 1980s, state of the art commercially-available wind turbines had rotor diameters of approximately 20 meters and power ratings of approximately 100 kW. In 2001, the average size of wind turbines installed in Germany was 1284 kW, and the US market utilized turbines of similar sizes in 2001. The trend toward larger turbines seems to be continuing and it is not clear when the manufacturers will stop increasing the sizes of their wind turbine designs.

As wind turbine rotors grow to larger sizes, the economics are adversely affected. The weight and cost of the blades 2, the hub 4, and other components of the turbine are proportional to the rotor diameter cubed. However, the swept area of the rotor, and hence the energy capture, are only proportional to the rotor diameter squared. Therefore, as the rotor gets larger, the energy produced gets more expensive. There are some economies of scale for larger turbines, such as the reduced number of foundations and the reduced amount of electrical cable required to interconnect the turbines. However, those economies of scale are outweighed for turbines above approximately 750 kW to 1 MW. The market for wind turbines has demanded increasingly large machines due to aesthetic concerns in Europe and because of the possibility for offshore wind projects where fixed costs are higher and economy of scale dictates larger turbines. As wind turbines continue to grow, their economics are likely to be adversely affected.

Figure 3:
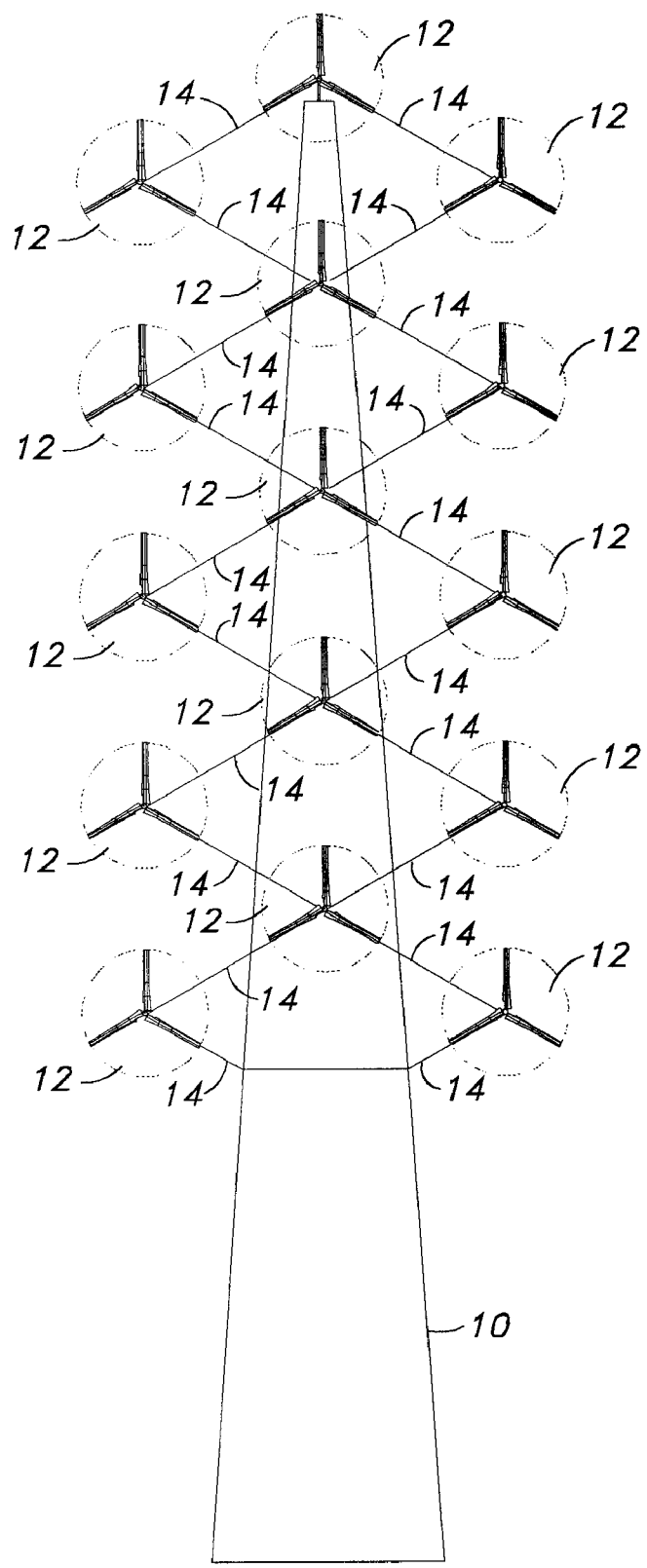
FIG. 3 is an elevation view of a first embodiment of the present invention.

FIG. 3 shows a first preferred embodiment of the wind turbine of the present invention. The wind turbine includes a tower 10 with a plurality of rotors 12 mounted on the tower at various heights. Each rotor 12 is attached to the tower 10 with a support structure 14. The tower 10 is shown as a tubular tower, although a truss-type tower could also work. The support structures 14 are shown as truss structures, although any suitable structural support would work as well and the support structures 14 could possibly be tubular monocoque type structure. An important aspect of the support structures 14 is that they must not negatively affect the wind flow through the rotors 12. Therefore, it is preferred that the support structures 14 be kept to a relatively small profile and that the structural members used have an aerodynamically efficient shape.

Figure 4:
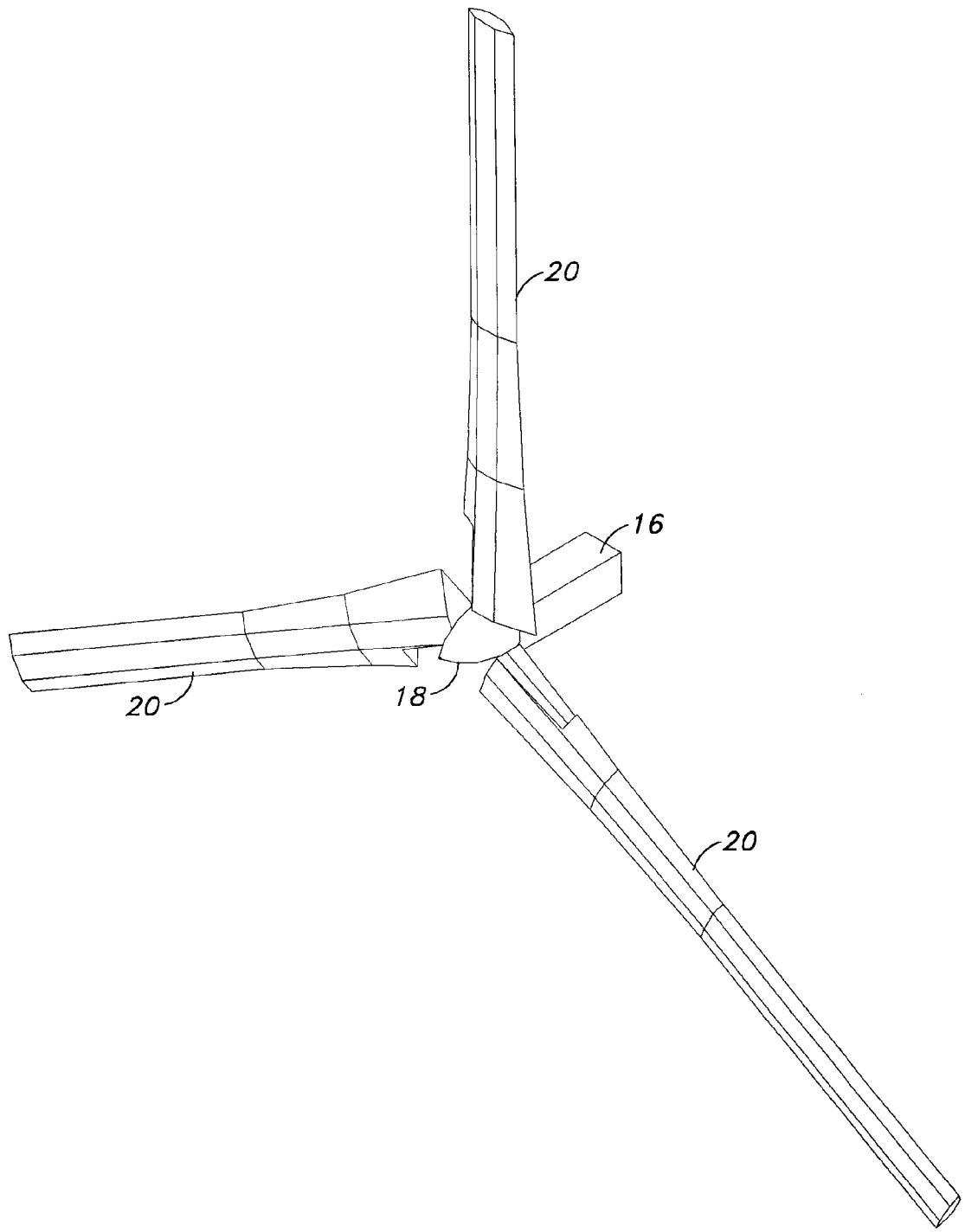
FIG. 4 is a three-bladed version of the rotor of the present invention.
Figure 5:
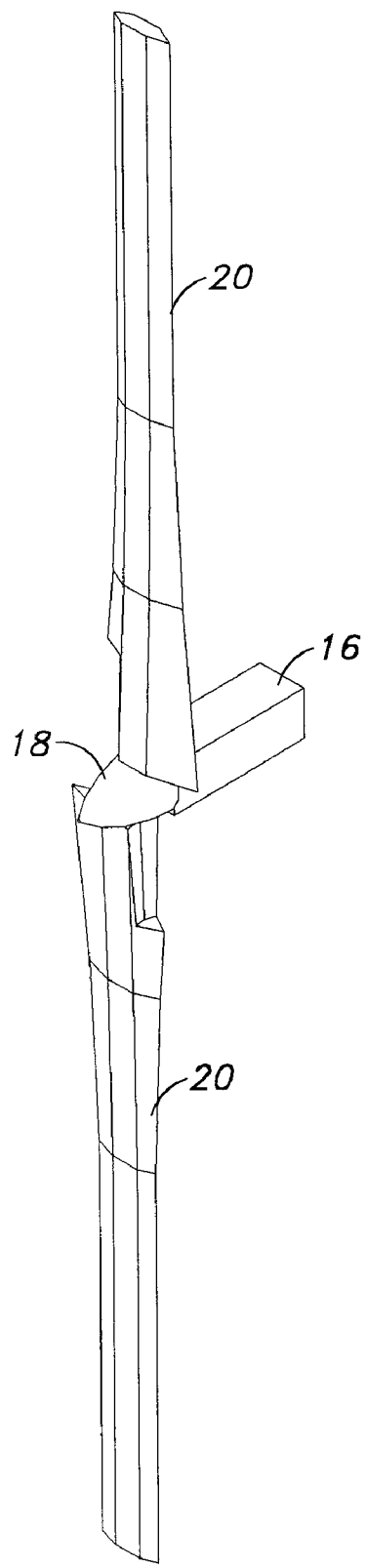
FIG. 5 is a two-bladed version of the rotor of the present invention.

Each rotor 12 consists of a nacelle 16 that is supported by a support structure 14, a hub 18 that is attached to a main shaft of a rotor that is located within the nacelle 16, and a plurality of blades 20 attached to the hub 18 for rotation therewith. Two different embodiments of the rotor 12 are shown in FIGS. 4 and 5. The embodiment shown in FIG. 4 includes three blades 20 attached to the hub 18 whereas the embodiment shown in FIG. 5 includes only two blades 20 attached to the hub 18. Either configuration can work well and the preferred embodiment may depend on the specific application. For instance, at sites where aesthetics are a concern, the three-bladed rotor as shown in FIG. 4 may be preferred. For offshore use, aesthetic concerns are not as important and it may be preferred to use the two-bladed rotor as shown in FIG. 5 while also using correspondingly higher tip speeds and lower solidities. The two-bladed turbine shown in FIG. 5 could be made with flexible blades 20 or with a teetered hub 18. The blades 20 are preferably glass fiber composite structures as used on conventional wind turbine rotors. They can use any airfoil that is suitable for use in a wind turbine blade. The airfoils are preferably similar to the ones described in U.S. Pat. Nos. 6,068,446, 5,562,420, and 5,417,548, the specifications of which are incorporated herein by reference. The rotors 12 may employ variable pitch for power regulation or the blades 20 may be designed to provide stall control.

The wind turbine of the present invention must yaw differently than prior art wind turbines. Rather than rotating the nacelle relative to the tower, the entire tower 10 is rotated to orient the rotors 12 with the wind direction. In order for the entire tower to yaw, it must be mounted to a bearing at the base of the tower. The bearing allows the tower to rotate relative to the tower foundation. The bearing at the tower base, in a preferred embodiment, takes the form of conventional truck or heavy machinery pneumatic tires and wheels that ride on a yaw track. The yaw track can be a surfaced roadway that is circular in shape and built around the base of the system. The yaw system will be discussed in more detail in reference to FIG. 6.

The rotors 12 of the wind turbine of the present invention are arranged at various heights. The rotors labeled with reference numeral 22 in FIG. 3 are the lowermost rotors. Above them are a row of rotors labeled 24. Rotors 26 are the middle row of rotors. Rotors 28 are the second from the top. Rotors 30 are the uppermost in the configuration shown in FIG. 3. In FIG. 3, the rotors within each of the rows 22, 24, 26, 28, 30 are staggered so that the middle rotor is a bit higher than the outer rotors. This allows the most dense packing of the rotors. However, as a matter of design choice, it might be preferable to have all three rotors within each row at the same height. Both of these configurations, as well as other configurations of the rotors, are considered to be within the scope of the present invention.

Each row of rotors experiences a different wind speed because of the effect of wind shear. By way of example only, each rotor could be 19 m in diameter, the lowermost row of rotors 22 could be situated at a height of 30 m above ground level, and the rows could be spaced from each other by 20 m so that the second row 24 is situated 50 m above ground level, the third row 70 m above ground level, the fourth row 90 m above ground level, and the fifth row 110 m above ground level. The size of the rotor diameters and their spacing are a matter of design choice, but these dimensions are provided as an illustrative example. For a wind shear exponent of 0.40, which is a typical value measured in the Midwest, the wind speed would vary by 68% from the bottom rotors 22 to the top rotors 30. The power in the wind would vary by 475% between the bottom rotors 22 and the top rotors 30.

By way of example, the lowermost row 22 of rotors 12 may experience an annual average windspeed of 6 m/s. An appropriate power rating for those rotors might be 100 kW. The average annual windspeed experienced by the uppermost row 30 of rotors 12 may experience an annual average windspeed of 10 m/s and have a rating of 300 kW. The rows in between would be rated at intermediate power levels. For instance, row 24 might be rated at 150 kW, row 26 at 200 kW, and row 28 at 250 kW. The exact ratings of each row of rotors would be determined based on wind characteristics for a specific site. The determination of the exact power rating for each row is a design choice that is within the ability of one of ordinary skill in the art.

In addition to customizing the power rating for each row of rotors, the present invention allows other design parameters to be selected for each row to optimize the performance of the rotor for the wind speed at that height. For instance, the amount of twist and taper in the blades can be selected for each row of rotors. Also, the rotor's solidity and tip speed can vary from row to row. Even the type of airfoil used in each row can be selected to optimize the rotors in that row to the wind speed at that height.

In addition to optimizing the aerodynamic performance of each row of rotors for the wind speed at that height, the structural strength of the rotors at each height must also be designed for the wind speeds that they experience. The top row 30 experiences the highest wind speeds and so the rotors in that row must be the heaviest and the strongest. The bottom row 22 experiences the lowest wind speeds and so the rotors in that row may be designed substantially lighter than the top row. The strength of intermediate rows should be designed appropriately for the wind speeds at the height of each respective row. The strength of the rotors in each row can be tailored by simply adding more material (i.e. more layers of glass in the blades and more steel in the shafts and gearbox) or by using different materials (i.e. adding carbon fibers to the blades in the upper rows).

In addition to, or instead of, selecting design parameters such as power rating, solidity, tip speed, twist, taper, etc, to optimize the performance of each row, the rotors 12 may be controlled individually for the wind speed that they experience. Each rotor 12 would ideally include a control anemometer mounted on top of the rotor's nacelle 16 to monitor the wind speed experienced by that rotor at each moment in time. The signal from each anemometer can be provided to a controller that adjusts the respective rotor's blade pitch angle and rotor speed based on the sensed wind speed. By individually controlling each rotor, all of the rotors can be operated at peak efficiency even if the wind speed varies dramatically from the bottom row 22 to the top row 30. Individual rotor control can also control the loads on each rotor. For instance, the top row of rotors may experience a high enough wind speed that they are above rated wind speed while the lower rows of rotors are still below rated. Therefore, the top row would be operated in a power control mode while the other rows are operated in a mode that maximizes power output. There may even be times when the wind speed is high enough to cause the top row or rows to be stopped due to high wind while the other rows are still able to continue running and producing power. The individual rotor control helps in low wind conditions as well because there will be periods of time when the wind speed is high enough for the top row or rows to begin producing power while the wind speed is still below cut-in for the lower rows.

Figure 6:
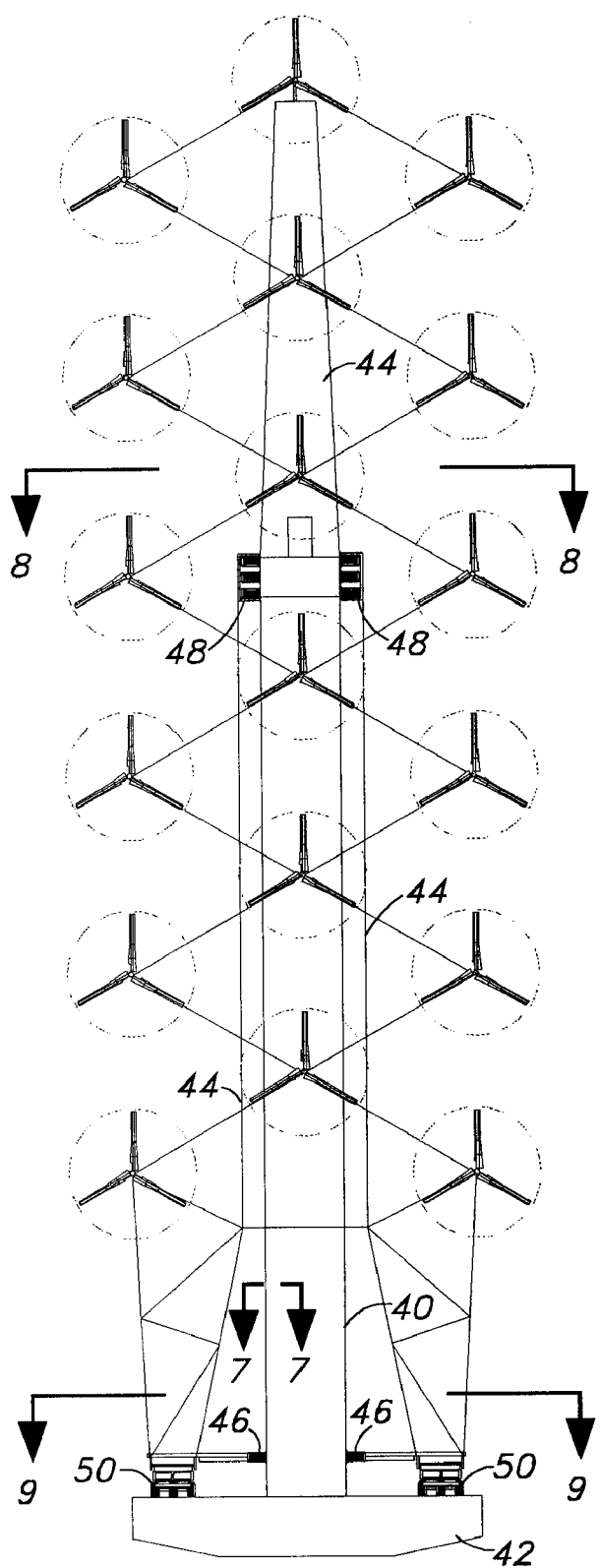
FIG. 6 is an elevation view of a second embodiment of the present invention.

One of the critical aspects of the present invention is the need to yaw the entire tower 10 as opposed to yawing only the nacelle in prior art wind turbines. There are several possible methods to achieve tower yawing. FIG. 6 shows one possible embodiment of a tower yaw system. The tower includes a fixed pole 40 that is rigidly attached to a foundation 42. The pole 40 must be of sufficient strength to support a significant portion of the bending moment at the base of the tower during high wind conditions. A rotating tower structure 44 is disposed around the fixed pole 40 to be concentric therwith. Rotor support structures 14 are rigidly attached to the tower structure 44. Tower structure 44 is mounted for rotation relative to fixed pole 40 about a vertical yaw axis. Horizontal components of the load on tower structure 44 are transmitted into pole 40 through bearings 46 and 48. The vertical component of the load on tower structure 44 is transmitted into foundation 42 through bogies 50. Bending moments are taken out through a couple between the horizontal forces in the two bearings 46, 48.

Figure 7:
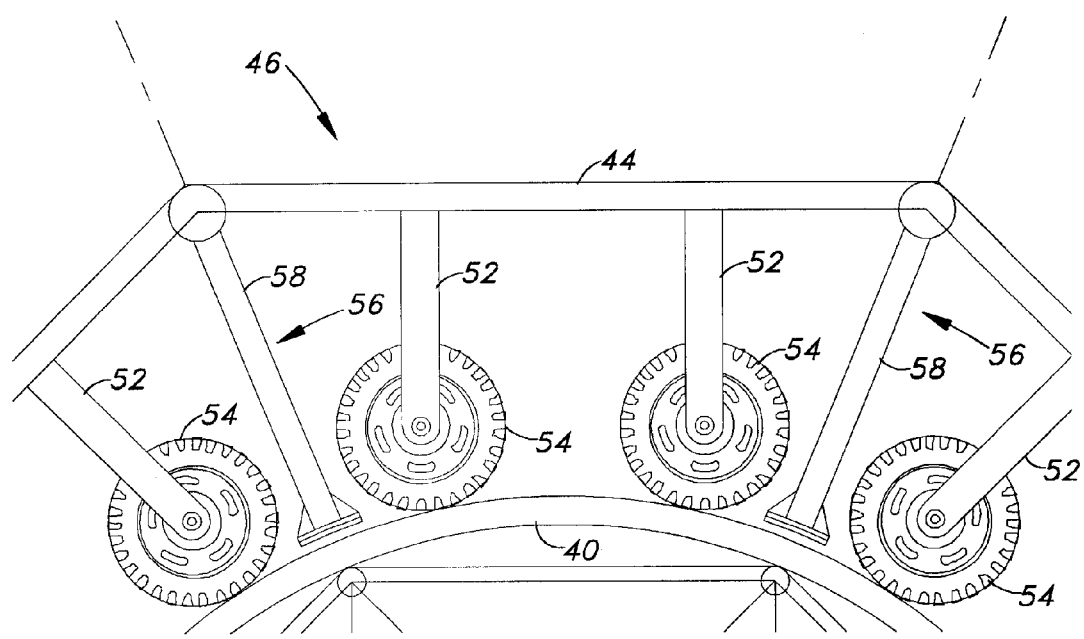
FIG. 7 is a sectional view along lines 7—7 of FIG. 6.

FIG. 7 shows a cutaway of the lower bearing 46. The tower 44 is shown as octagonal in shape, although it could also be circular in shape or it could be a truss type structure. Rigidly attached to the tower structure 44 are a plurality of struts 52. On each strut 52, there is a roller 54. The rollers 54 bear against the side of the pole 40 to transmit horizontal forces thereto. Rotation of the rollers 54 allows the tower structure 44 to yaw smoothly around the pole 40. The rollers 54 are preferably commercially available pneumatic tires. Interposed between the rollers 54 there are a plurality of brake devices 56. The brake devices 56 each include a strut 58 and a brake pad 60. The strut 58 is constructed to be extensible and retractable. Extension and retraction of the strut 58 can be achieved by a hydraulic or pneumatic cylinder or other suitable actuator. As the strut 58 is extended, the brake pad 60 engages the side of the pole structure 40. Friction between the brake pad 60 and the pole 40 prevents yawing of the tower 44. When the strut 58 is retracted, the brake pad loses contact with the side of the pole 40 and yawing is possible. The upper bearings 48 are similar in construction to the lower bearing 46 except that there are three sets of upper bearings 48 to transmit the higher loads at the top of pole 40. The brake devices 56 may optionally be omitted from the top bearings 48 if the brake devices 56 associated with the lower bearings 46 are strong enough to prevent yawing on their own.

Figure 8:
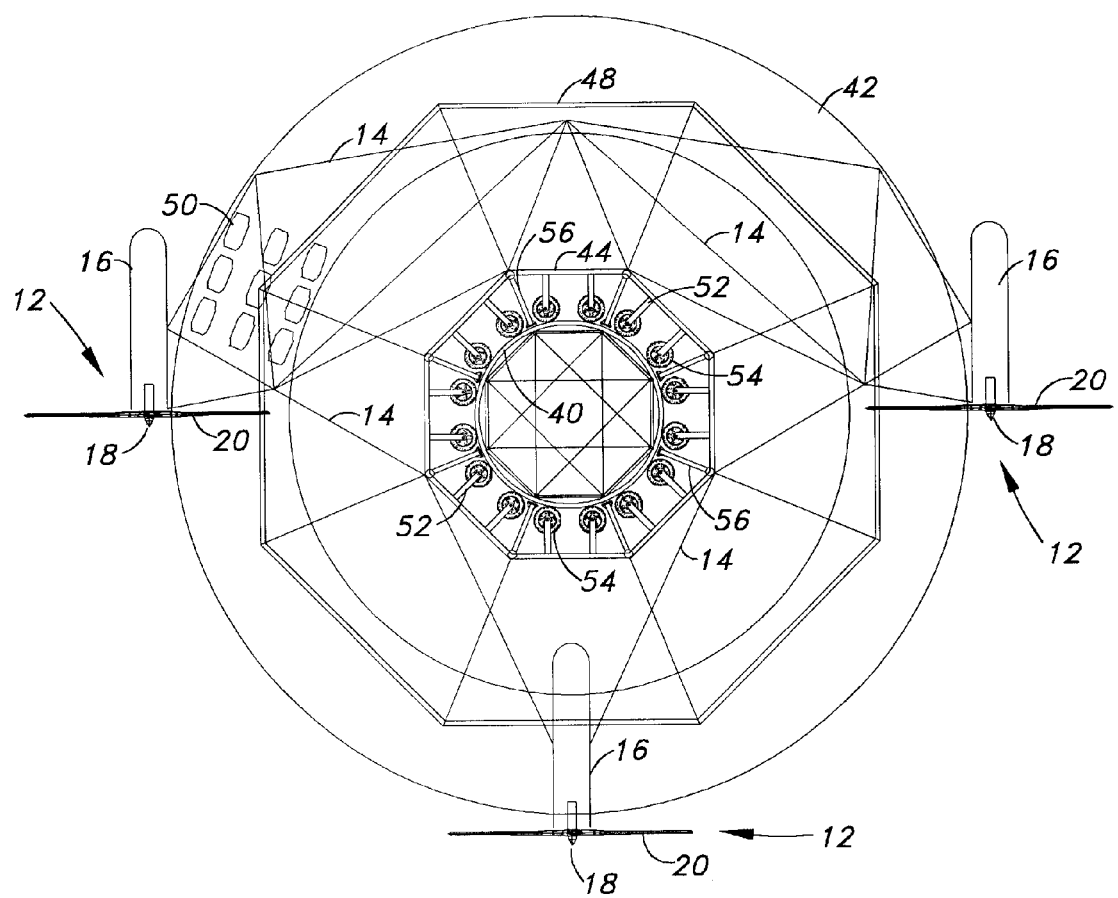
FIG. 8 is a sectional view along lines 8—8 of FIG. 6.

FIG. 8 shows a cross sectional view of the wind turbine along lines 8—8 in FIG. 6. The upper bearings 48 can be seen to include a total of 16 struts and rollers 52, 54. The upper bearing 48 also includes a set of brake devices 56, although these devices could optionally be omitted at the upper bearing station. There are three sets of bearings at the upper bearing station 48. The extra sets of bearings 48 at the upper station are to transmit the higher lateral forces at the top of the pole 40 compared to the bottom of the pole. As shown in FIG. 8, the rotor support structures 14 are truss structures that support the rotors 12 in the appropriate locations. Alternatively, the support structures 14 may be tubular monocoque structures. One rotor 12 is located in front of the tower 44 and two of the rotors 12 are located to the sides of the tower 44. This creates a staggered arrangement in which the center rotor is somewhat in front of the side rotors. The staggered arrangement of the rotors may enhance aerodynamic performance of the overall system by augmenting the wind flow through the side rotors.

Figure 9:
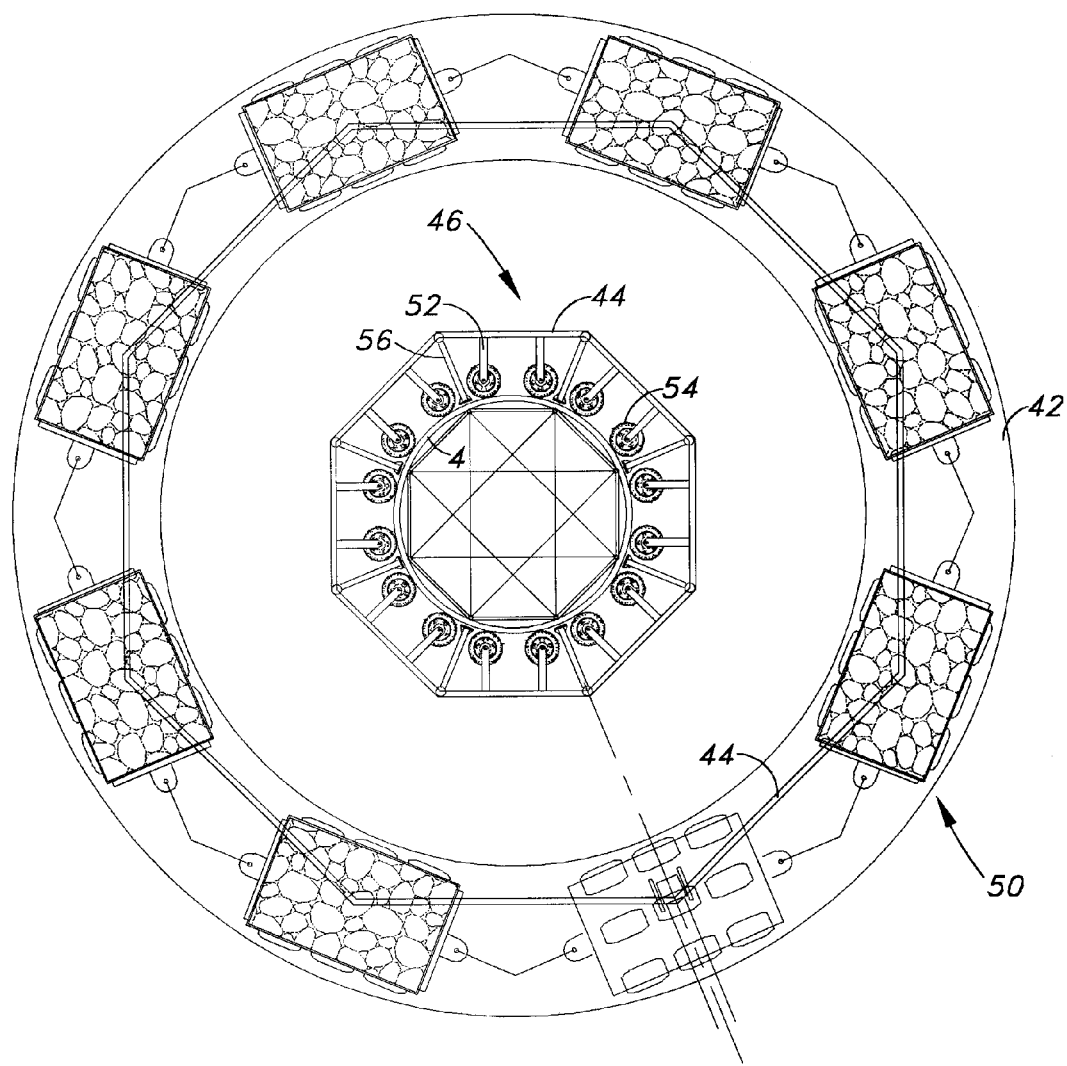
FIG. 9 is a sectional view along lines 9—9 of FIG. 6.

FIG. 9 shows a cross sectional view of the wind turbine along lines 9—9 in FIG. 6. The lower bearings 46 are similar in construction to the upper bearings 48 except that a smaller number of bearings are required to transmit the horizontal force at the bottom of pole 40. FIG. 9 shows in greater detail the bogies 50 that transmit vertical forces into the foundation 42. Preferably the foundation 42 includes a blacktop upper surface similar to conventional roadway surfaces. The bogies 50 each consist of a body 58 that is attached to and provides support for the tower 44. Each bogie body 58 is supported on a plurality of wheels 60. The bogie wheels 60 ride on the blacktop surface of foundation 42. The bogies 50 are attached to one another to form a train in a circular shape. As the bogies 50 ride on their wheels 60 they allow the tower 44 to yaw. This provides a very strong, very simple, and very inexpensive yaw bearing. This yaw system is expected to be far superior to the extremely large high precision roller bearings required for the yaw drives of large multi-megawatt wind turbines of conventional design. The bodies 58 of the bogies 50 are filled with ballast material 62. The ballast material 62 could be concrete, rock, slurry, or any other inexpensive material with relatively high density. The weight of the ballast material 62 in the bogies 50 provide a reaction moment to counteract the overturning moment on tower 44 that is caused by thrust forces on rotors 12. If enough ballast material 62 is provided in the bogies 50 and if the diameter of the circular train of bogies 50 is large enough, then the reaction moment provided by the bogies 50 may be sufficient to withstand all of the overturning moment on the tower 44. If the overturning moment is not fully reacted by the weight of the bogies 50, then some of the moment will be supported by the horizontal reactions of bearings 46 and 48 on pole 40.

Figure 10:
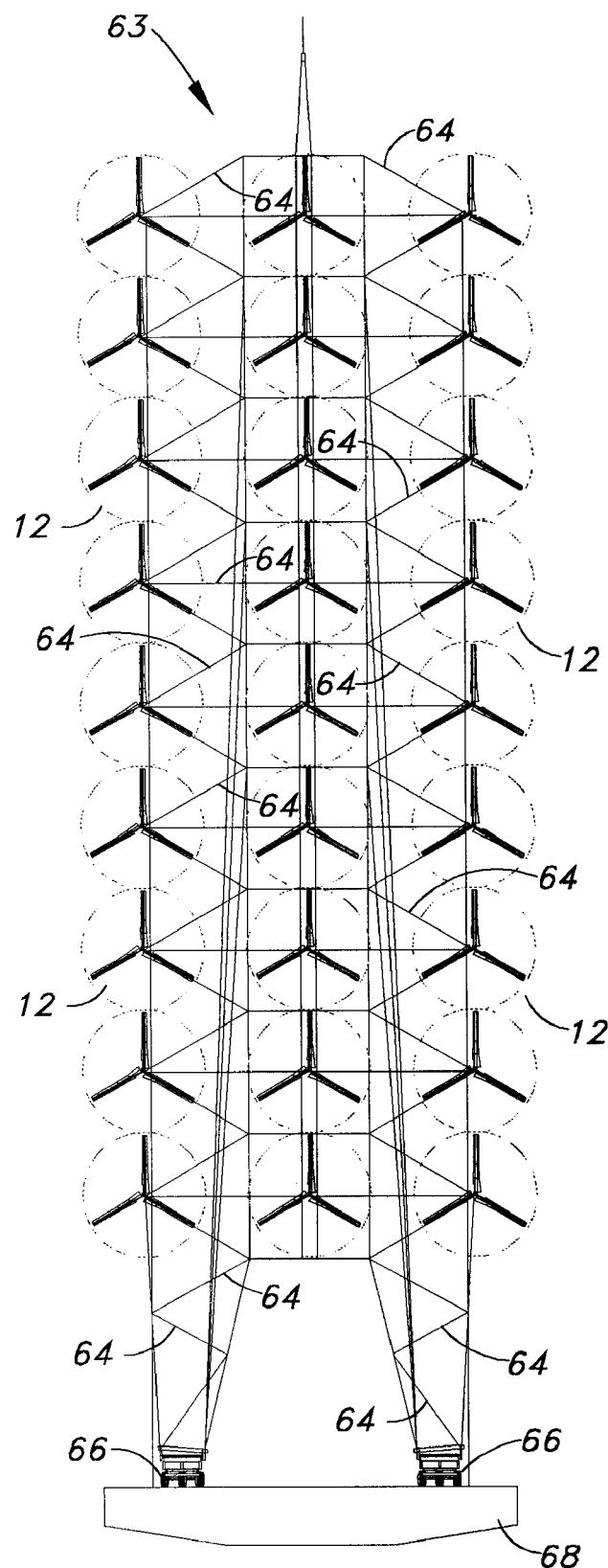
FIG. 10 is a front elevation view of a third embodiment of the present invention.

FIG. 10 shows another embodiment of the invention. In this embodiment there are 27 rotors arranged in 9 rows. In addition to the different number of rotors, the rotors within each row are not staggered in height. There may be structural or other design considerations that lead to an arrangement in which the rotors within each row are not staggered. However, by staggering the rotors as shown in FIGS. 3 and 6, it is possible to achieve a tighter packing of rotors. In addition to the modified arrangement of the rotors, the embodiment shown in FIG. 10 differs from that of FIGS. 6 through 9 in that the tower structure is a truss tower rather than a tubular tower. The rotors 12 are supported by a frame 63 made up of a plurality of tension-compression members 64. The size, shape, number, and arrangement of the tension-compression members 64 should be designed to provide adequate support for the static and dynamic loads that the rotors 12 exert. Exact details of the truss tower are not given here but it is within the ability of one of ordinary skill in the art to design an adequate tower frame.

The truss tower frame 63 is supported on bogies 66. The bogies are similar in construction and function to those described above in reference to FIG. 9. The bogies 66 ride on pneumatic tires on foundation 68. The bogies support both the horizontal and vertical components of force from frame 63. They also provide the sole reaction to overturning moments because the embodiment shown in FIG. 10 does not include a central stationary pole structure or any central bearings. Because the bogies 66 must provide all of the reaction to overturning moments, it is important for them to be sufficiently heavy.

Figure 11:
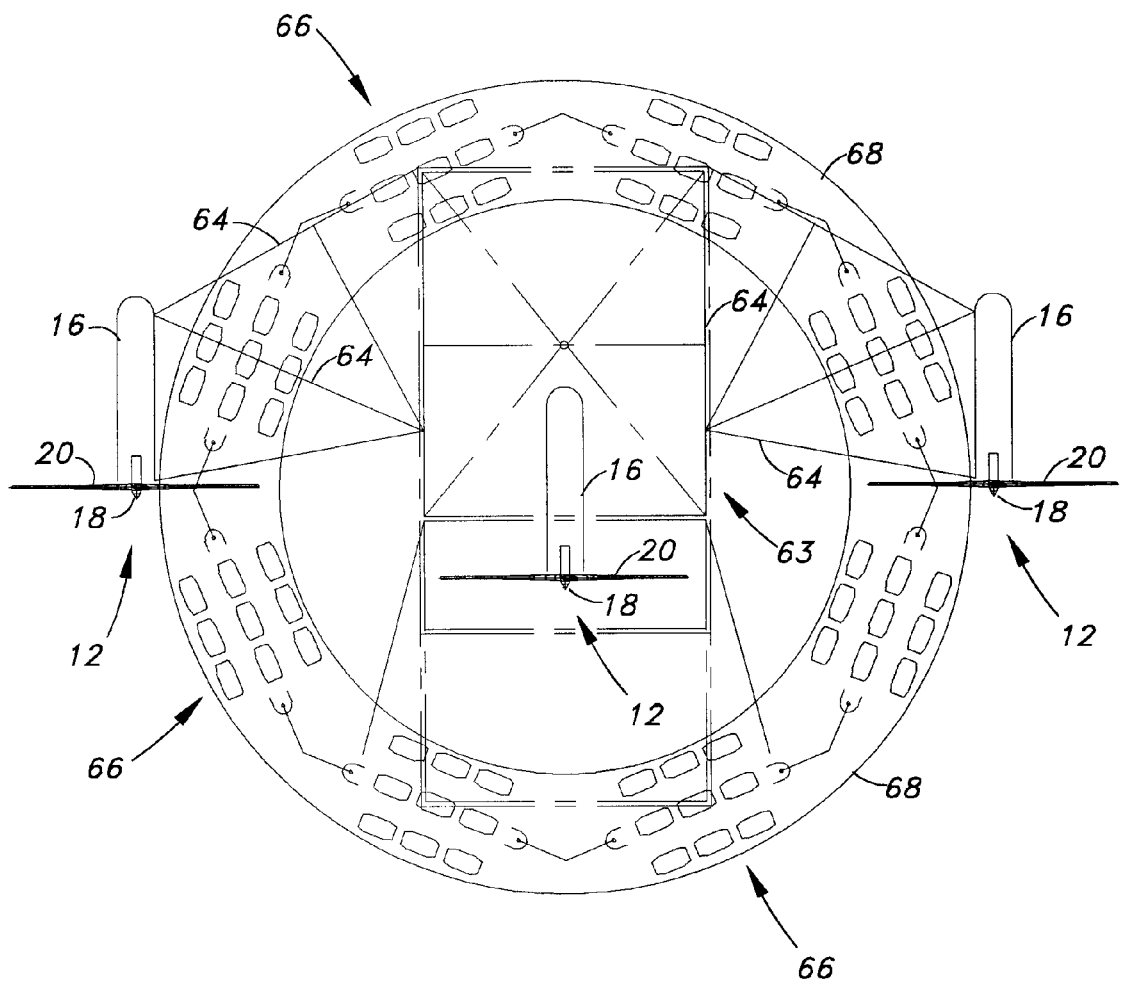
FIG. 11 is a plan view of the third embodiment of the present invention.

FIG. 11 shows a top view of the same embodiment shown in FIG. 10. It can be seen that the rotors are staggered so that the center rotor is farther forward than the side rotors. This may provide some aerodynamic performance advantage. However, for structural design considerations or for other reasons, it may be preferably to have all of the rotors arranged in a common plane. The side rotors are supported by wings of truss tension and compression members 64 that extend laterally from the main frame 63.

Figure 12:
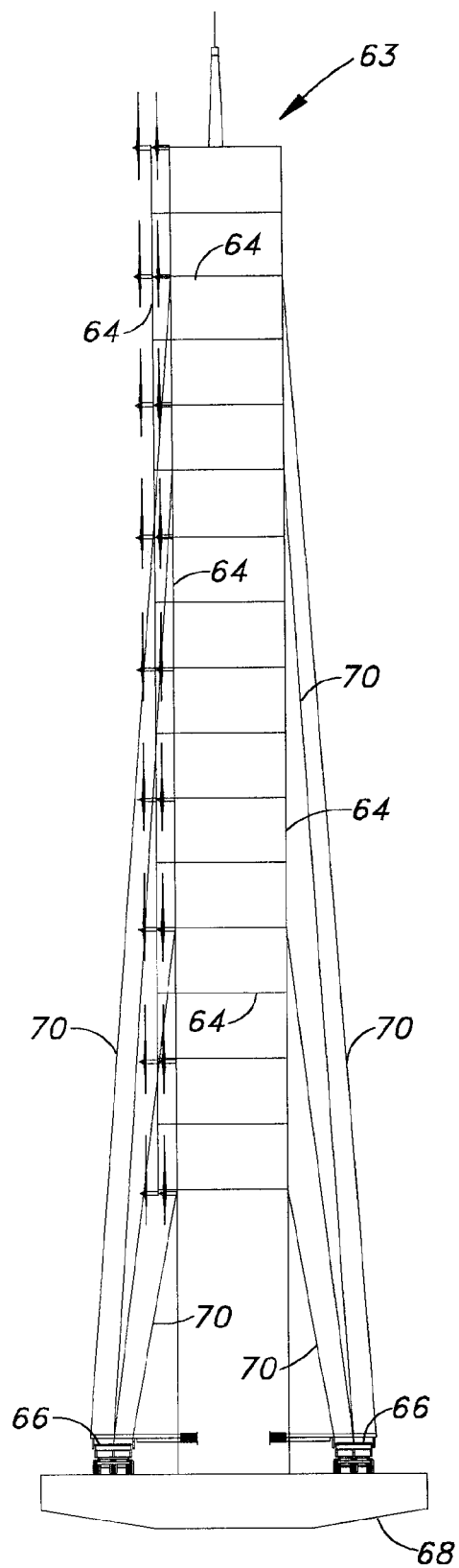
FIG. 12 is a side elevation view of the third embodiment of the present invention.

FIG. 12 shows a side view of the same embodiment shown in FIG. 10. It can be seen that there are a plurality of guy cables 70 that extend from the front and back of the truss frame 63 to transmit loads from the frame into the fore and aft bogies 66. Tension in the forward guy cables 70 provides the primary reaction against overturning moments.

On top of the truss frame 63, as shown in FIGS. 10 and 12, there is a lightning rod 72. The lightning rod 72 is tall enough so that all of the rotors 12 are within its cone of protection. The lightning rod attracts any nearby lightning and directs the current safely through frame 63 and into the ground through foundation 68. A suitable electrical conductor should be provided between the frame 63 and the foundation 68 to adequately ground the entire system. Recent experience in the wind industry has shown that lightning damage can be a significant problem on very large wind turbines. Prior art wind turbines are constrained in that a blade is always the tallest part of the turbine and it cannot easily be protected from lighting. The use of smaller rotors mounted on a frame structure allows a lightning rod to be placed higher than the top of the tallest blade, thereby giving adequate protection to the blades.

Figure 13:
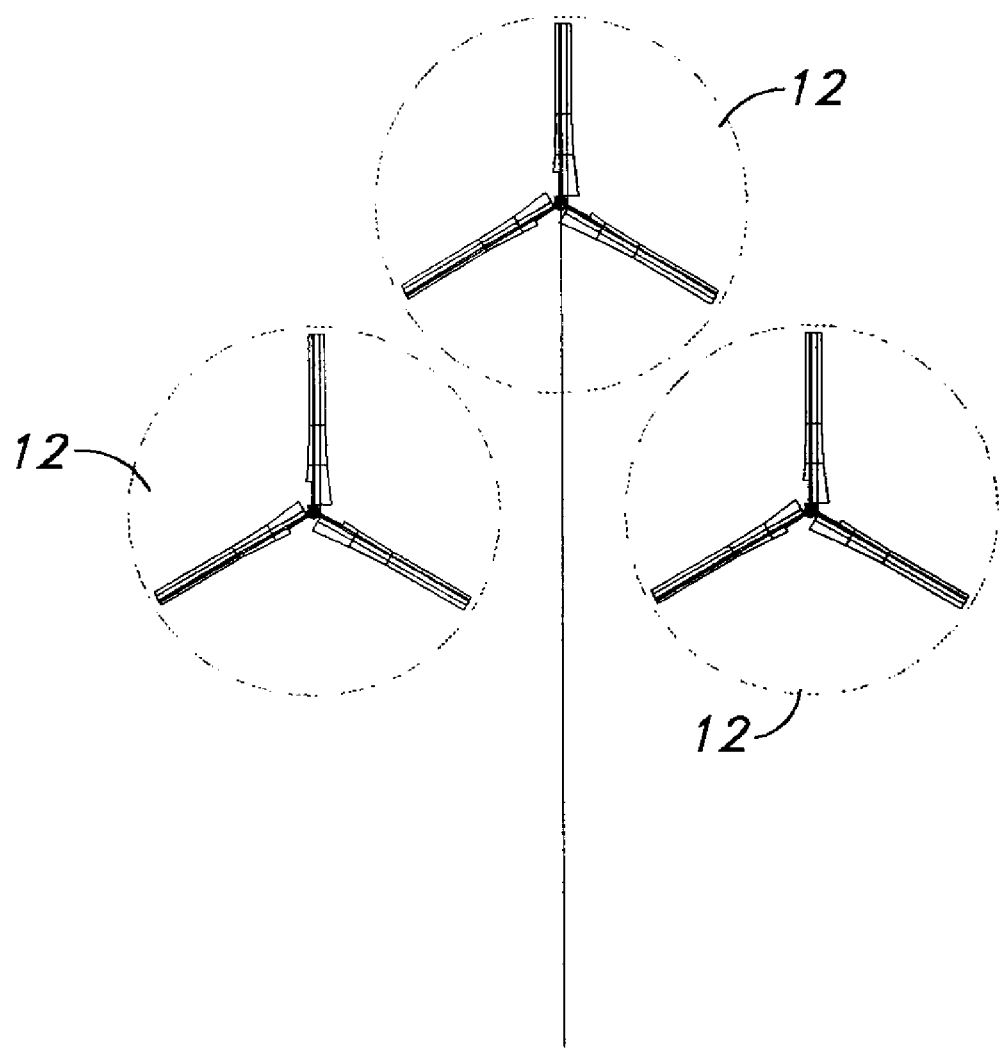
FIG. 13 is a schematic view of a fourth embodiment of the present invention.
Figure 14:
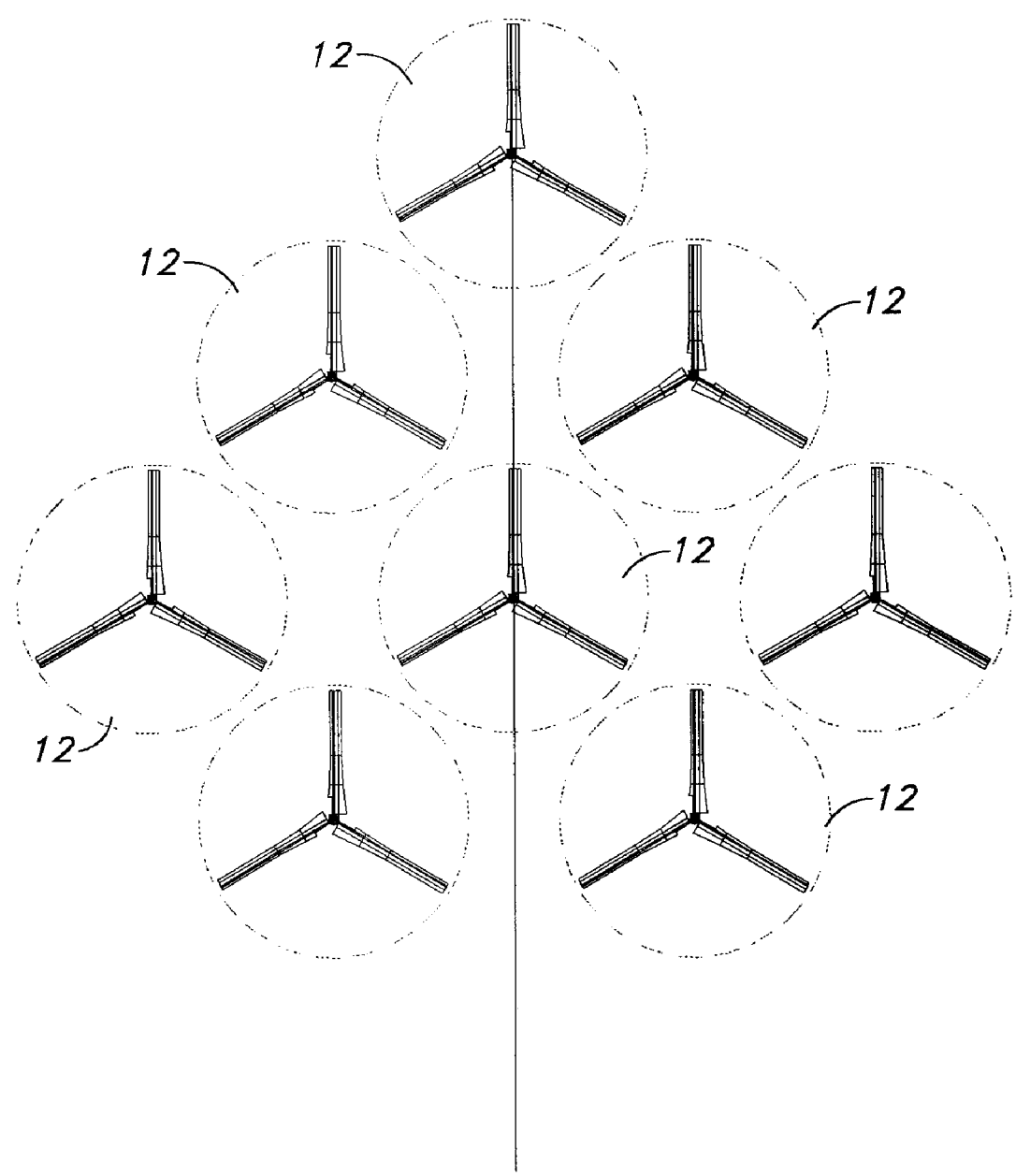
FIG. 14 is a schematic view of a fifth embodiment of the present invention.
Figure 15:
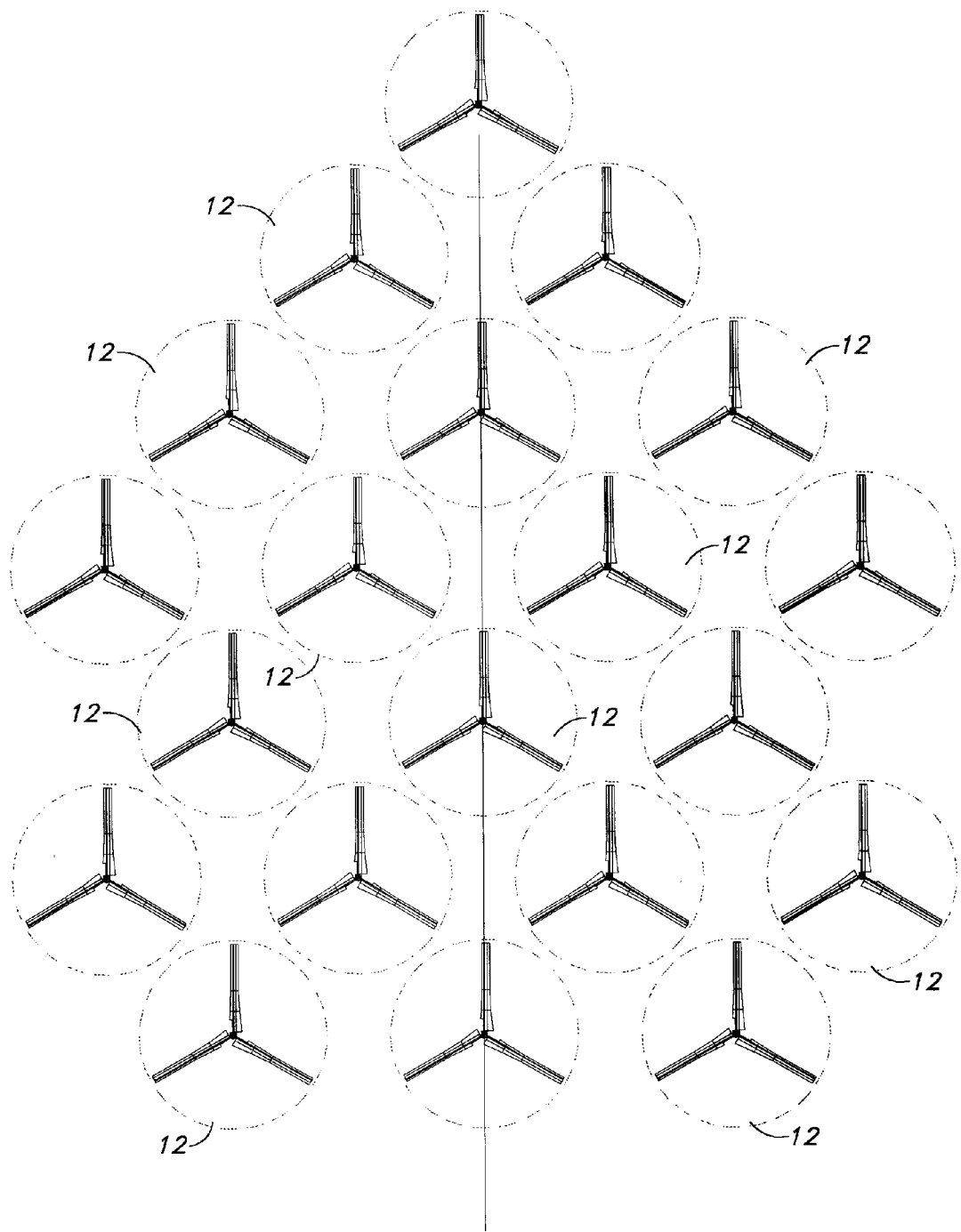
FIG. 15 is a schematic view of a sixth embodiment of the present invention.

FIG. 3 shows an embodiment of the invention with 15 rotors in staggered rows and FIG. 10 shows an embodiement of the invention with 18 rotors in straight rows. However, there are many other possible configurations of quantity of rotors and arrangement of the rotors. For instance, FIG. 13 shows a configuration with only three rotors. FIG. 14 shows an arrangement with 8 rotors. FIG. 15 shows an arrangement with 20 rotors. Many other configurations can be conceived of and they are all considered to be within the scope of the present invention. The number and arrangement of rotors is only limited by the ability of the structural engineer to design a support structure that will adequately support the rotors and provide yawing of the system. In each of the configurations, however, it is important that each of the rotors be optimized for the wind speed that it experiences.

Figure 16:
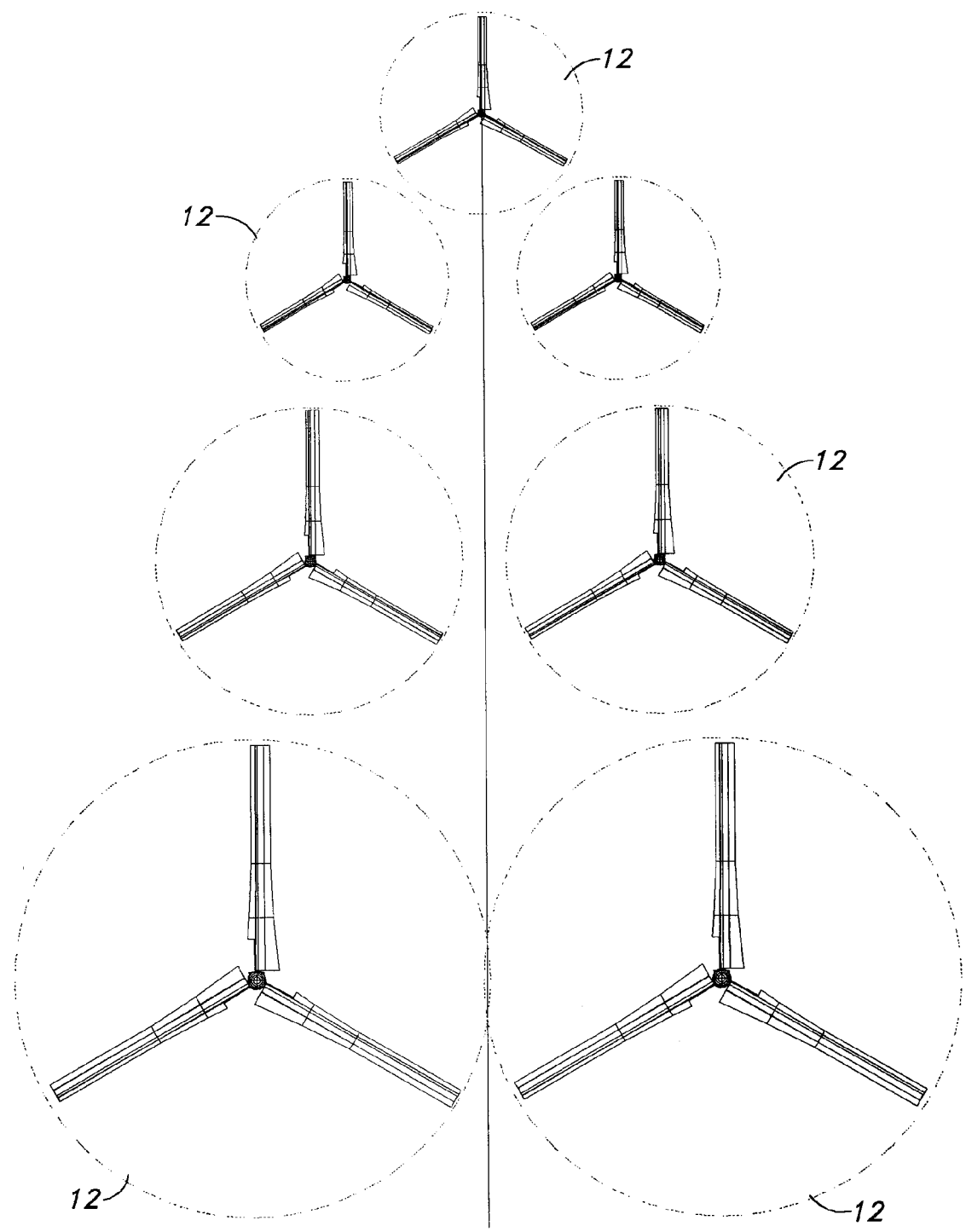
FIG. 16 is a schematic view of a seventh embodiment of the present invention.

Another possible embodiment of the present invention is shown in FIG. 16. Here there are 7 rotors arranged in rows at four different heights. The rotor diameter is different at each row so that each row of rotors is optimized for the wind speeds that it experiences. The lowest row of rotors experiences the lowest wind speed and so its rotors are the largest. It is expected that the power ratings of all of the rotors are the same in the embodiment shown in FIG. 16. It is possible that one might want to design this embodiment of turbine with different power ratings for each row, but by making the power rating consistent for all of the rotors, it is possible to use interchangeable gearboxes and generators.

The wind turbine according to the present invention has several additional advantages over the prior art. Since multiple rotors are turning at disparate rotational speeds, the vibrational excitation of the structure is spread across several frequencies rather being concentrated on a single frequency. This reduces the structural loads due to structural dynamics and lowers the chance of low cycle fatigue failure. Another advantage of the present invention is that it can easily be transported. Very large megawatt-scale wind turbines have extremely large blades and nacelles that are quite difficult and expensive to transport. This is particularly a problem if the parts must be delivered to a remote area with tight curves in the road or with low overpasses. Since the individual components of the present invention are much smaller than those of prior art wind turbines, the entire system can be packaged for shipment in standard 60 foot sea containers.

A potentially very attractive application of the present invention is for offshore generation of wind energy. Rather than using bogies or some other system to yaw the tower, the entire tower can be supported on a hull in the water. Since the hull can rotate easily in the water, yawing of the tower is not a problem. The hull that supports the tower would be secured by a tether that is connected to an anchor on the ocean floor. In this manner, it would be possible to deploy offshore arrays of wind turbines in very deep water.

One of the issues that the present invention creates is summation of power from the individual rotors. Generally, it is not a problem for each rotor to generate electrical power and for the electrical power from each of the rotors to be collected into a single transmission line. However, there is still a question of whether to convert the varying frequency at each rotor into 60 Hz electricity (50 Hz in Europe) and to sum the resulting 60 Hz power, or whether to feed the varying frequency power from each rotor into a single power electronic converter at the base of the tower and convert all of the power into 60 Hz power at once. Another possibility is to generate DC power at each individual rotor and to combine the DC power which can then be inverted into 60 Hz AC power. Any of these methods of summing power would work and each of them could provide advantages in certain applications. One other possibility would be to provide a system of mechanical drive train linkages so that mechanical power from each of the rotors is combined to drive a single electric generator.

An intriguing use of the present invention would be to electrolyze water to generate hydrogen. The hydrogen could then be transported for use elsewhere in a fuel cell or in a gas-turbine generator set or in spark ignition engines. This method of power production could be particularly advantageous for use offshore and where the wind turbines are located in remote locations where the winds are especially energetic. The product to be sent back to market could include gaseous or liquid hydrogen. It could also include methanol synthesized from $CO_2$ scrubbed out of seawater or the atmosphere plus the electrolyzer-produced hydrogen. The product could also include high octane gasoline created by further hydrogenation (dehydration) of the methanol or, as anhydrous ammonia, synthesized from $N_2$ distilled from the atmosphere, plus hydrogen. If the wind turbine of the present invention is used to electrolyze water into hydrogen, or to create some other product through a chemical process, then the issue of summation of power from the individual rotors is solved. Each rotor could include its own electrolyzer and the hydrogen produced at each rotor could simply be combined and bottled at the tower base. Combined DC power at the tower base could be used to power electrolyzers sited there.

While preferred embodiments of the invention have been shown and described, it will be apparent to those skilled in the art that various modifications may be made in these embodiments without departing from the scope of the invention. Therefore, it is intended that the invention not be limited to the particular embodiments disclosed but that the scope of the invention be defined by the following claims.

What is claimed is:

1. A wind turbine comprising:

a tower;

a plurality of rotors attached to said tower at a plurality of heights wherein each rotor is optimized for the, wind speed at the height at which it is attached wherein said rotor has a plurality of blades and the ratio of the planform area of said blades to the swept area of each said rotor is selected based on the annual average wind speed at the height at which it is attached.

2. A wind turbine comprising:

a tower;

a plurality of rotors attached to said tower at a plurality of heights wherein each rotor is optimized for the wind speed at the height at which it is attached wherein each said rotor has a rotor diameter that is selected based on the annual average wind speed at the height at which it is attached.

3. A method of extracting energy from wind comprising:

providing a tower;

supporting a plurality of rotor driven turbines on said tower at a plurality of heights; and optimizing each said rotor driven turbine for the wind speed at the height at which it is supported wherein the step of optimizing each said rotor driven turbine comprises providing each said rotor with a plurality of blades and selecting the ratio of the planform area of said blades to the swept area of each said rotor based on the annual average wind speed at the height at which it is supported.

4. A method of extracting energy from wind comprising:
providing a tower;
supporting a plurality of rotor driven turbines on said tower at a plurality of heights; and
optimizing each said rotor driven turbine for the wind speed at the height at which it is supported wherein the step of optimizing each said rotor driven turbine comprises selecting a rotor diameter based on the annual average wind speed at the height at which it is supported.

* * * * *